United States Patent
Dongare et al.

(10) Patent No.: US 8,957,250 B2
(45) Date of Patent: Feb. 17, 2015

(54) PROCESS FOR CATALYTIC DEHYDRATION OF LACTIC ACID TO ACRYLIC ACID

(75) Inventors: Mohan Keraba Dongare, Pune (IN); Shubhangi Bhalchandra Umbarker, Pune (IN); Samadhan Tanaji Lomate, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/115,064

(22) PCT Filed: May 16, 2012

(86) PCT No.: PCT/IB2012/052449
§ 371 (c)(1),
(2), (4) Date: Jan. 27, 2014

(87) PCT Pub. No.: WO2012/156921
PCT Pub. Date: Nov. 22, 2012

(65) Prior Publication Data
US 2014/0155653 A1   Jun. 5, 2014

(30) Foreign Application Priority Data
May 16, 2011   (IN) .......................... 1419/DEL/2011

(51) Int. Cl.
*C07B 35/00* (2006.01)
*C07C 51/377* (2006.01)

(52) U.S. Cl.
CPC .................................. *C07C 51/377* (2013.01)

USPC ........................................................ 562/599

(58) Field of Classification Search
None
See application file for complete search history.

(56) References Cited

U.S. PATENT DOCUMENTS 2,859,240 A   11/1958   Holmen

OTHER PUBLICATIONS

Hong et al., Applied Catalysis A: General, Elsevier Science, Feb. 15, 2011, vol. 396, No. 1, pp. 194-200.*
Or Lee et al., Catalysis Communications, Elsevier Science, Amsterdam, NL, Sep. 25, 2010, pp. 1176-1180, vol. 11, No. 15.*
International Search Report received in PCT/IB/2012/052449 dated Oct. 22, 2012.
Hong et al, "Efficient and Selective Conversion of Methyl Lactate to Acrylic Acid Using Ca(PO)Ca(PO) Composite Catalysts", Applied Catalysis A: General, Elsevier Science, Feb. 15, 2011, vol. 396, No. 1, pp. 194-200.
Lee J M et al, "Efficient Dehydration of Methyl Lactate to Acrylic Acid Using Ca3(PO4)2-Si02 Catalyst", Catalysis Communications, Elsevier Science, Amsterdam, NL, Sep. 25, 2010, pp. 1176-1180, vol. 11, No. 15.

* cited by examiner

*Primary Examiner* — Karl J Puttlitz
(74) *Attorney, Agent, or Firm* — Foley & Lardner LLP

(57) ABSTRACT

Disclosed herein is an improved process for the catalytic dehydration of lactic acid to acrylic acid. More particularly, the present invention discloses catalytic dehydration of lactic acid to acrylic acid with high selectivity and yield for acrylic acid using calcium phosphate (CP) catalyst with varying Ca/P ratio optionally modified with 5 wt % sodium.

2 Claims, 2 Drawing Sheets

PROCESS FOR CATALYTIC DEHYDRATION OF LACTIC ACID TO ACRYLIC ACID

FIELD OF THE INVENTION

The present invention relates to an improved process for the catalytic dehydration of lactic acid to acrylic acid. More particularly, it relates to catalytic dehydration of lactic acid to acrylic acid with high selectivity and yield for acrylic acid using calcium phosphate (CP) catalyst with varying Ca/P ratio.

BACKGROUND AND PRIOR ART OF THE INVENTION

Utilization of renewable raw materials for the production of value added chemicals is one of the main R&D activities all over the world to overcome the dependence on depleting fossil fuels. Lactic acid is one of the renewable chemical obtained from fermentation of biomass and is being considered as one of the important raw material for the production of value added chemicals. Further, acrylic acid and acrylates comprise a class of materials having potential industrial applications especially in the field of polymers and co polymers. The relatively high cost of acrylates as a result of the methods of preparation available in the prior art and other inefficiencies limits the use of this important material.

Catalytic dehydration of lactic acid to acrylic acid is being investigated in both academic and industrial laboratories with limited success. When heated at moderate temperatures, lactic acid readily converts to lactides or polylactic acid. At higher temperatures, lactic acid decompose to acetaldehyde, carbon dioxide and water, a property typical of alpha hydroxy acids.

Heterogeneous catalysts have been used by scientific community to bring about catalytic dehydration of lactic acid to acrylic acid however, low conversion of lactic acid and lower selectivity for acrylic acid as well as catalyst deactivation highlight the main drawbacks in their use.

U.S. Pat. No. 4,786,756 describes a process for the catalytic conversion of lactic acid and/or ammonium lactate to acrylic acid which comprises contacting a mixture of water and lactic acid and/or ammonium lactate in the vapor phase with solid aluminum phosphate which has been treated with an aqueous inorganic base and calcined at a temperature in the range from 300° C. to 650° C. The base is selected from aqueous ammonium hydroxide and potassium hydroxide. With lactic acid as the feed, the acrylic acid yield of 43.3% has been reported at 340° C.

U.S. Pat. No. 4,729,978 discloses inert metal oxide selected from the group consisting of silica, titania and the alumina phosphate salt is selected from the group consisting of $NaH_2PO_4$, $Na_2HPO_4$, $K_2HPO_4$, $KH_2PO_4$, $Li_2HPO_4$, $LiH_2PO_4$, $LaPO_4$, $Mg_3(PO_4)_2$ and $Ca(H_2PO_4)_2$. Further, the base is selected from the group consisting of $Na_2CO_3$, $NaHCO_3$, $KHCO_3$, $K_2CO_3$, $LiCO_3$, $CaCO_3$, $MgCO_3$ and $La(CO_3)_3$ for conversion of lactic acid to acrylic acid. With Lactic acid as the feed, acrylic acid yield of 58% with a selectivity of 65% has been claimed.

Efficient dehydration of methyl lactate to acrylic acid using $Ca_3(PO_4)_2$—$SiO_2$ catalyst by Jong-Min Lee et. al (Catalysis Communications, Volume 11, Issue 15, 25 Sep. 2010, Pages 1176-1180) describes a series of catalysts consisting of $Ca_3(PO_4)_2$ supported on $SiO_2$ (silicate, colloidal silica and fumed silica) and $Ca_3(PO_4)_2$—$SiO_2$ (silicate) with different loadings of $Ca_3(PO_4)_2$ (70 to 95 wt. %) was prepared by sol-gel and wet-impregnation methods. All the catalysts were found to be active in the vapor phase dehydration of methyl lactate (ML) to give mainly acrylic acid (AA), methyl acrylate (MA). Among the catalysts, $Ca_3(PO_4)_2$—$SiO_2$(silicate) of (80:20 wt. %) was found to be an efficient catalyst in the dehydration of Methyl Lactate, which gave 73.6% conversion of Methyl Lactate with selectivity for Acrylic Acid and Methyl Acrylate together (77.1%).

U.S. Pat. No. 2,859,240 discloses the catalytic production of acrylic acid from lactic acid which comprises the steps of (1) bringing lactic acid into contact with a dehydration catalyst consisting essentially of at least one member of the group consisting of the sulfates and phosphates of metals of groups I and II which are at least-as high as cadmium in the electromotive series, at a temperature within the range of 200° C. to 600° C. and (2) separating acrylic acid from at least some of the reaction products. It further discloses that the salts of the alkaline earth metals, especially of calcium, strontium and barium provide the highest yields and are preferred. The practice of this invention is not limited to fixed bed catalysts, but may be carried out with a fluidized bed when such conditions are advantageous. Furthermore, in example 32 granules of a mixture of tricalcium phosphate and sodium pyrophosphate Na4P2O7 in-25:1 molar ratio were employed as the catalyst mass to convert lactic acid to acrylic acid with 48-52% yield.

References may be made to Engineering Science Paper titled "Research on microwave assisted Dehydration of Lactic acid to Acrylic Acid" dated 25 Feb. 2012 discloses the use of disodium hydrogen phosphate and potassium hydrogen phosphate as promoter along with Calcium sulphate and copper sulphate.

There, however, remains a need to improve upon the existing catalytic process of conversion of lactic acid to acrylic acid which can result in 100% conversion of lactic acid and is highly selective to acrylic acid with minimum production of acetaldehyde and other products.

OBJECTS OF THE INVENTION

Main object of the present invention is to provide an improved catalytic process for dehydration of lactic acid to acrylic acid.

Another object of the present invention is to provide catalytic dehydration of lactic acid to acrylic acid with high selectivity and yield for acrylic acid using calcium phosphate (CP) catalyst with varying Ca/P ratio.

Yet another object of the present invention is to provide an improved catalytic process for dehydration of lactic acid to acrylic acid, with minimum production of acetaldehyde.

Yet another object of the present invention is to provide a catalytic process which has high selectivity and productivity for acrylic acid from lactic acid.

SUMMARY OF THE INVENTION

Accordingly, present invention provides an improved process of dehydrating lactic acid to acrylic acid in a quartz fixed bed reactor, with 100% conversion of lactic acid and high selectivity for acrylic acid upto 70% characterized in using stable calcium phosphate as dehydrating catalyst wherein calcium to phosphorous ratio varying in the range of 1.5 to 1.9 optionally modified with 5 wt % sodium and the said process comprising the steps of:
  i. preheating the catalyst in a fixed-bed reactor at a temperature in the range of 370 to 380° C. for 20 to 40 minute under highly pure nitrogen;

ii. passing the vapors of 50-80 wt % preheated lactic acid solution through the catalyst bed by nitrogen in a fixed-bed reactor and condensing the vapors to obtain acrylic acid.

In an embodiment of the preset invention, source of the sodium used is selected from the group consisting of $Na_2HPO_4.2H_2O$, $Na_3PO_4.12H_2O$ or $NaNO_3$.

In another embodiment of the preset invention, the catalyst with Ca/P ratio of 1.5 at pH 7 is modified using different sodium precursors to obtain 5 wt % Na on calcium phosphate.

In yet another embodiment of the preset invention, the catalyst is Ca/P ratio of 1.5 at pH 7, modified using different sodium precursors to obtain 5 wt % Na on calcium phosphate, the catalyst is promoter-free.

In yet another embodiment of the preset invention, the catalyst used in the instant invention can be modified using different sodium precursors such as disodium hydrogen phosphate ($Na_2HPO_4.2H_2O$), trisodium phosphate ($Na_3PO_4.12H_2O$ or sodium nitrate ($NaNO_3$).

In yet another embodiment of the preset invention, the life of the catalyst thus obtained is tested for almost 120 hr to check the stability of the catalyst for the desired reaction conditions.

DETAILED DESCRIPTION OF THE INVENTION

Figure 1:
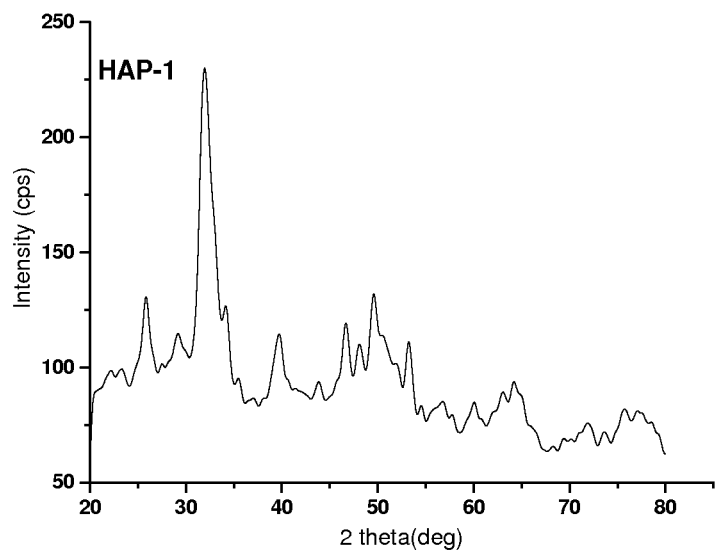
FIG. 1: depicts HAP-1 XRD pattern
Figure 2:
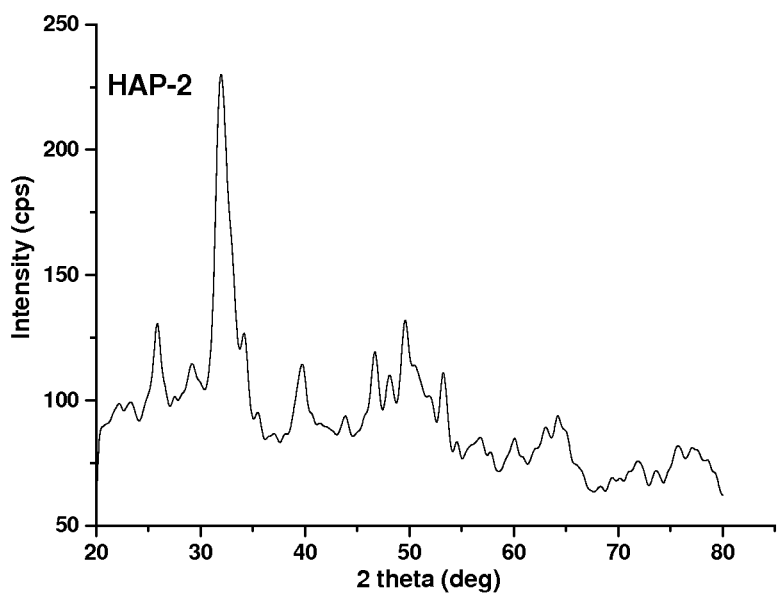
FIG. 2: depicts HAP-2 XRD pattern
Figure 3:
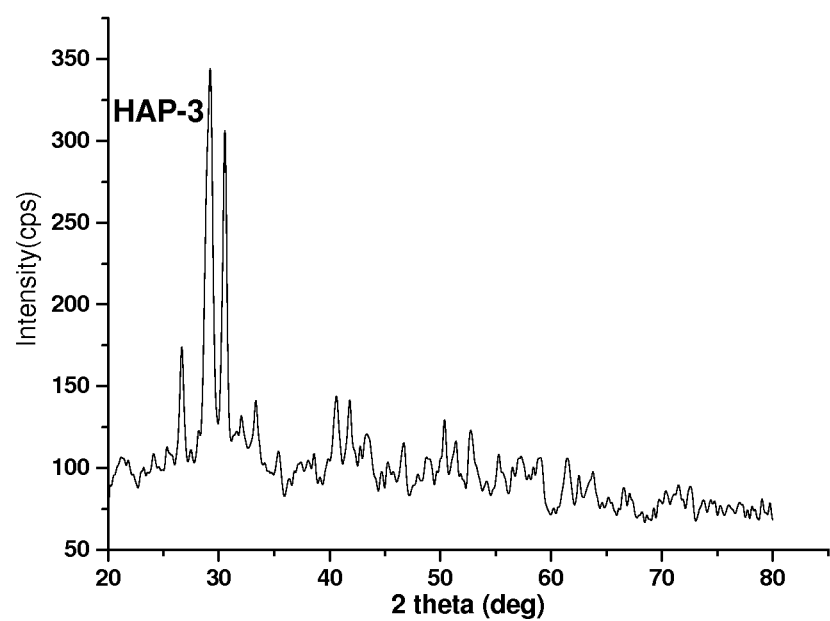
FIG. 3: depicts HAP-3 XRD pattern

The present invention relate to an improved catalytic process for dehydration of lactic acid to acrylic acid. The catalytic dehydration of lactic acid with high conversion and selectivity for acrylic acid according to the present invention is much higher than the ones reported in the prior art.

The catalyst used in the current invention for dehydration process is heterogeneous in nature and the catalyst life is also quite good. The catalyst used for the dehydration process is a stable calcium phosphate (CP) having calcium to phosphorous ratio varying in the range of 1.5-1.9 which leads to 100% conversion of lactic acid and also high selectivity i.e. 60 to 80% for acrylic acid. The conversion and selectivity for acrylic acid remains more or less constant for a long time as per laboratory experimentation.

Present invention provides an improved process of dehydrating lactic acid to acrylic acid in a quartz fixe bed reactor, with 100% conversion of lactic acid, using stable calcium phosphate as catalyst wherein calcium to phosphorous ratio varies in the range of 1.5-1.9, characterized in the following steps;

1. preheating the catalyst, in the catalyst bed, with 20 mesh to a temperature of 375° C. for 0.5 h under highly pure nitrogen (30 ml/min); and
2. passing the vapors of preheated lactic acid solution (50-80 wt %) through the catalyst bed (WHSV=3 $h^{-1}$) by nitrogen and condensing the vapors to obtain the product.

According to the process, the dehydration of lactic acid is carried out in a quartz fixed-bed reactor of 15 mm inner diameter. The catalyst calcium phosphate with Ca/P ratio in the range of 1.5-1.9 and with 20 mesh is charged in the middle section of the reactor, with quartz wool packed in both ends. Porcelain beads are placed above the catalyst bed in order to preheat and vaporize the feed. Before subjecting the catalyst for dehydration reaction, the catalyst is preheated to a temperature of 375° C. for 30 minutes under high purity N2 (30 ml/min). This is followed by pumping the feed stock, 50-80 wt % solution of Lactic acid, into the preheating zone (WHSV=3-5 $h^{-1}$). The vapors are then driven through the catalyst bed by nitrogen where dehydration of lactic acid takes place. The products are condensed and analyzed by GC using GC (Perkin Elmer) equipped with a FFAP capillary column and FID detector.

The lactic acid conversion is 100% with 60-80% selectivity for acrylic acid and about 15-35% selectivity for acetaldehyde.

The calcium phosphate catalyst of the present invention is prepared by a process comprising co-precipitation of calcium nitrate with diammonium phosphate at specified pH range where Ca:P ratio varies from 1.5 to 1.9.

Calcium phosphate (CP) catalyst with varying Ca/P ratio from 1.5 to 1.9 is prepared by the precipitation method. The calcium nitrate [$Ca(NO_3)_2$] solution is added drop wise with constant stirring to the alkaline solution of diammonium hydrogen phosphate [$(NH_4)_2HPO_4$] to form white precipitate of calcium phosphate. The precipitate is filtered, washed and dried in an oven at 150° C. for 8 to 12 hr and calcined at 600° C. for four hours to obtain calcium phosphate catalyst.

The life of the catalyst thus obtained is tested for almost 120 hr to check the stability of the catalyst for the desired reaction conditions. There was no appreciable change in conversion and selectivity. The catalyst of the instant invention is stable and can be recycled and reused. Three catalysts are prepared by maintaining different pH with different Ca/P ratio as given in examples below.

The catalyst used in the instant invention can be modified using different sodium precursors such as disodium hydrogen phosphate ($Na_2HPO_4.2H_2O$), trisodium phosphate ($Na_3PO_4.12H_2O$ or sodium nitrate ($NaNO_3$). Accordingly, solution of desired concentration of calcium nitrate, disodium hydrogen phosphate and diammonium hydrogen phosphate are prepared in deionised water. Ammonia gas is passed in all the three solutions separately till pH of each solution becomes 7. The disodium hydrogen phosphate solution is added drop-wise to the diammonium hydrogen phosphate solution. To this solution calcium nitrate solution was added drop wise with constant stirring. A thick white precipitate formed which is filtered, washed and dried in an oven at 150° C. for 8 to 12 hr.

This dried calcium phosphate modified with sodium is calcined at 600° C. for four hours.

The catalyst with Ca/P ratio of 1.5 at pH 7 is modified using different sodium precursors to obtain 5 wt % Na on calcium phosphate.

The process of the invention, wherein the catalyst is Ca/P ratio of 1.5 at pH 7, modified using different sodium precursors to obtain 5 wt % Na on calcium phosphate, the catalyst is promoter-free.

The invention demonstrates efficiency of catalyst selectivity and conversion data of lactic acid to acrylic acid as mentioned in examples.

EXAMPLES

Following examples are given by way of illustration therefore should not construed to limit the scope of the invention.

Example 1

Process of Preparation of Catalyst

HAP-1 (Ca/P=1.9) catalysts were prepared by the precipitation method. Analytical grade calcium nitrate [$Ca(NO_3)_2$]

and diammonium hydrogen phosphate [(NH$_4$)$_2$HPO$_4$] was used for preparation of catalyst. Calcium nitrate solution (41.89 g in 125 ml water) and diammonium hydrogen phosphate solutions (12.35 g in 125 ml) were prepared in deionised water. Ammonia gas was passed in both the solutions till pH 12. The calcium nitrate solution was added drop wise with constant stirring to the solution of diammonium hydrogen phosphate. A thick white precipitate of hydroxyapatite was formed which was filtered, washed and dried in an oven at 150° C. for 10 hr. The dried calcium phosphate was calcined at 600° C. for four hours to yield 9.5 g of catalyst.

Example 2

HAP-2 (Ca/P=1.65) catalysts were prepared by the precipitation method. Analytical grade calcium nitrate [Ca(NO$_3$)$_2$] and diammonium hydrogen phosphate [(NH$_4$)$_2$HPO$_4$] was used for preparation of catalyst. Calcium nitrate solution (40.12 g in 125 ml water) and diammonium hydrogen phosphate solutions (13.60 g in 125 ml water) were prepared in deionised water. Ammonia gas was passed in both the solutions till pH 10. The calcium nitrate solution was added drop wise with constant stirring to the solution of diammonium hydrogen phosphate. A thick white precipitate of calcium phosphate was formed which was filtered, washed and dried in an oven at 150° C. for 8 hr. The dried calcium phosphate was calcined at 600° C. for four hours to yield 9.7 g catalyst.

Example 3

HAP-3 (Ca/P=1.5) catalysts were prepared by the precipitation method. Analytical grade calcium nitrate [Ca(NO$_3$)$_2$] and diammonium hydrogen phosphate [(NH$_4$)$_2$HPO$_4$] was used for preparation of catalyst. Calcium nitrate solution (38.35 g in 125 ml water) and diammonium hydrogen phosphate solutions (14.52 g in 125 ml water) were prepared in deionised water. Ammonia gas was passed in both the solutions till pH 7. The calcium nitrate solution was added drop wise with constant stirring to the solution of diammonium hydrogen phosphate. A thick white precipitate of calcium phosphate was formed which was filtered, washed and dried in an oven at 150° C. for 8 to 12 hr. This dried calcium phosphate was calcined at 600° C. for four hours to yield 9.4 g catalyst.

The three different catalysts at varying pH and Ca/P molar ratio prepared by the process according to examples 1-3 are given in Table 1 below.

TABLE 1

| Catalyst | P$^H$ | Ca/P molar ratio |
|---|---|---|
| HAP-1 | 12 | 1.9 |
| HAP-2 | 10 | 1.65 |
| HAP-3 | 7 | 1.5 |

The catalyst HAP-3 was modified by adding 5 wt % Na using different sodium precursors as follows:

Example 4

NaHAP-3a (5 wt % Na on HAP3 with Ca/P=1.5) catalysts were prepared by the precipitation method. Analytical grade disodium hydrogen phosphate (Na$_2$HPO$_4$.2H$_2$O), calcium nitrate [Ca(NO$_3$)$_2$] and diammonium hydrogen phosphate [(NH$_4$)$_2$HPO$_4$] was used for preparation of the catalyst. Calcium nitrate (36.95 g in 125 ml water), disodium hydrogen phosphate (1.911 g in 50 ml water) and diammonium hydrogen phosphate solutions (13.77 g in 125 ml water) were prepared in deionised water. Ammonia gas was passed in all the three solutions till pH 7. The disodium hydrogen phosphate solution was added drop wise to the diammonium hydrogen phosphate solution. To this solution calcium nitrate solution was added drop wise with constant stirring. A thick white precipitate was formed which was filtered, washed and dried in an oven at 150° C. for 8 to 12 hr. This dried calcium phosphate was calcined at 600° C. for four hours to yield 9.5 g catalyst.

Example 5

NaHAP-3b (5 wt % Na on HAP3 with Ca/P=1.5) catalysts were prepared by the precipitation method. Analytical grade trisodium phosphate (Na$_3$PO$_4$.12H$_2$O), calcium nitrate [Ca(NO$_3$)$_2$] and diammonium hydrogen phosphate [(NH$_4$)$_2$HPO$_4$] was used for preparation of catalyst. Calcium nitrate (36.95 g in 125 ml water), trisodium phosphate (2.75 g in 50 ml water) and diammonium hydrogen phosphate (13.77 g in 125 ml water) solutions were prepared in deionised water. Ammonia gas was passed in all the three the solutions till pH 7. The trisodium phosphate solution was added dropwise to the diammonium hydrogen phosphate solution. To this solution calcium nitrate solution was added drop wise with constant stirring. A thick white precipitate was formed which was filtered, washed and dried in an oven at 150° C. for 12 hr. This dried calcium phosphate was calcined at 600° C. for four hours to yield 9.7 g catalyst.

Example 6

NaHAP-3c (5 wt % Na on HAP3 with Ca/P=1.5) catalysts were prepared by the precipitation method. Analytical grade sodium nitrate (NaNO$_3$), calcium nitrate [Ca(NO$_3$)$_2$] and diammonium hydrogen phosphate [(NH$_4$)$_2$HPO$_4$] was used for preparation of catalyst. Calcium nitrate (36.95 g in 125 ml water), sodium nitrate (1.84 g in 125 ml water) and diammonium hydrogen phosphate (13.77 g in 125 ml water) solutions were prepared in deionised water. Ammonia gas was passed in all the three the solutions till pH 7. The sodium nitrate solution was added dropwise to the calcium nitrate solution. This solution was added drop wise with constant stirring to the solution of diammonium hydrogen phosphate. A thick white precipitate was formed which was filtered, washed and dried in an oven at 150° C. for 8 to 12 hr. This dried calcium phosphate was calcined at 600° C. for four hours to yield 9.8 gm catalyst.

The three different modified catalysts at pH 7 and Ca/P molar ratio of 1.5 prepared by the process according to examples 4-6 are given in Table 2 below.

TABLE 2

| Catalyst | P$^H$ | Na Loading (wt %) | Na source | Ca/P molar ratio |
|---|---|---|---|---|
| NaHAP-3a | 7 | 5 | Na$_2$HPO$_4$•2H$_2$O | 1.5 |
| NaHAP-3b | 7 | 5 | Na$_3$PO$_4$•12 H$_2$O | 1.5 |
| NaHAP-3c | 7 | 5 | NaNO$_3$ | 1.5 |

Example 7

Process for Conversion of Lactic Acid to Acrylic Acid Using Catalyst of Invention The dehydration of LA to AA over HAP-1 catalyst was tested in a quartz fixed-bed reactor of 15 mm inner diameter.

Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapours was driven through the catalyst bed by nitrogen. The products were condensed and then analyzed by GC. The lactic acid conversion was 100% with 50% selectivity for acrylic acid and about 45% selectivity for acetaldehyde.

Example 8

The dehydration of LA to AA over HAP-2 catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapours was driven through the catalyst bed by nitrogen. The products were condensed and then analyzed by GC. The lactic acid conversion was 100% with 55% selectivity for acrylic acid and about 40% selectivity for acetaldehyde.

Example 9

The dehydration of LA to AA over HAP-3 catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapors was driven through the catalyst bed by nitrogen. The products were condensed and then analyzed by GC. The lactic acid conversion was 100% with 60% selectivity for acrylic acid and about 35% selectivity for acetaldehyde.

Example 10

The dehydration of LA to AA over HAP-3 catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (80 wt % solution of LA) was pumped into the preheating zone first (WHSV=3 $h^{-1}$) and then the vapors was driven through the catalyst bed by nitrogen. The products were condensed and then analyzed by GC. The lactic acid conversion was 85% with 60% selectivity for acrylic acid and about 35% selectivity for acetaldehyde.

Example 11

The dehydration of LA to AA over HAP-3 catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=4.5 $h^{-1}$) and then the vapors was driven through the catalyst bed by nitrogen. The products were condensed and then analyzed by GC. The lactic acid conversion was 89% with 60% selectivity for acrylic acid and about 35% selectivity for acetaldehyde.

Example 12

The dehydration of LA to AA over NaHAP-3a catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapors was driven through the catalyst bed by nitrogen. The products were condensed and then analyzed by GC. The lactic acid conversion was 100% with 64% selectivity for acrylic acid and about 30% selectivity for acetaldehyde.

Example 13

The dehydration of LA to AA over NaHAP-3b catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapors was driven through the catalyst bed by nitrogen. The products were condensed and then analyzed by GC. The lactic acid conversion was 100% with 70% selectivity for acrylic acid and about 25% selectivity for acetaldehyde.

Example 14

The dehydration of LA to AA over NaHAP-3c catalyst was tested in a quartz fixed-bed reactor of 15 mm inner diameter. Catalyst (4 g) with 20 mesh was charged in the middle section of the reactor, with quartz wool packed in both ends. Porcelain beads were placed above the catalyst bed in order to preheat and vaporize the feed. Before studying the catalytic activity for the dehydration reaction, the catalyst was preheated at desired reaction temperature (375° C.) for 0.5 h under high purity $N_2$ (30 ml/min). Then the feedstock (50 wt % solution of LA) was pumped into the preheating zone first (WHSV=3 $h^{-1}$) and then the vapors was driven through the catalyst bed by nitrogen. The products were condensed and then analyzed by GC. The lactic acid conversion was 100% with 64% selectivity for acrylic acid and about 30% selectivity for acetaldehyde.

The selectivity and conversion data are given below in Table 3 below

| Sr. No. | Catalyst | Conversion, % | Selectivity % AA | Acetaldehyde | Other |
|---|---|---|---|---|---|
| 1 | HAP-1 | 100 | 50 | 40 | 10 |
| 2 | HAP-2 | 100 | 55 | 36 | 9 |
| 3 | HAP-3 | 100 | 60 | 33 | 7 |
| 4 | NaHAP-3a | 100 | 64 | 30 | 6 |
| 5 | NaHAP-3b | 100 | 70 | 25 | 5 |
| 6 | NaHAP-3c | 100 | 64 | 30 | 6 |

Comparison with Prior Art Process is Tabulated Below: (Table 4)

| Criteria | 1419DEL2011 | PCT1216 Communications, Volume, 25 Apr. 2009, Pages 1345-1349 | CN 101352688 |
|---|---|---|---|
| Title | IMPROVED PROCESS FOR CATALYTIC DEHYDRATION OF LACTIC ACID TO ACRYLIC ACID | POTASSIUM MODIFIED NaY: A Selective And Durable Catalyst For Dehydration Of Lactic Acid To Acrylic Acid | CATALYST FOR PRODUCING ACROLEIC ACID BY LACTIC ACID DEWATERING AND REACTION TECHNIQUE |
| Catalyst | Calcium Phosphate (HAP—Hydroxyapatite) & NaHAP (HAP having 5% Na) ($Na_2HPO_4$ used as catalyst modifier) | NaY zeolite with potassium modified | Inorganic porous material vector-Silica aluminium molecular sieve, phosphorus aluminium molecular sieve and acive metal component is rare earth elements |
| Process | Catalyst was tested in quartz fixed-bed reactor of 15 mm inner diameter ↓ Catalyst (4 g) with 20 meshes was charged in the middle section of the reactor with quartz wool packed in both ends Porcelain beads placed above the catalyst bed in order to preheat and vaporize the feed ↓ Catalyst preheated at 375° C. for 0.5 h under high $N_2$ (30 ml/min) ↓ Feedstock (50 wt % lactic acid aqueous solution) pumped into preheating zone (WHSV = 3 h−1) and vapours was driven through the catalyst bed by nitrogen ↓ Products condensed and analyzed by GC | Catalyst was tested in quartz fixed-bed reactor of 8 mm inner diameter ↓ Catalyst (1.5 g) with 20 meshes was charged in the middle section of the reactor with quartz wool packed in both ends ↓ Porcelain beads placed above the catalyst bed in order to preheat and vaporize the feed ↓ Catalyst preheated at 375° C. for 0.5 h under high $N_2$ (30 ml/min) ↓ Feedstock (29 wt % lactic acid aqueous solution) pumped into preheating zone (WHSV = 3 h−1) and vapors was driven through the catalyst bed by nitrogen ↓ Products condensed and analyzed by GC | In the 30 cm quartz tube fixed bed reactor loads the catalyst in the length ↓ Passes over the speed of flow is the 20 ml/min carrier gas nitrogen ↓ Feedstock (30 wt % lactic acid solutions) was pumped by using the micro metering pump, lactic acid speed of flow 0.05 ml/min and carries on the response under 280-400.deg. C. temperature. |
| Acrylic Acid Selectivity | 60-70% | 60% (catalyst activity is not stable, after 5 hr conversion dropped to 97% & selectivity dropped to 35%) | 63% |
| Conversion % | 100 | 100 | 100% |
| Acetaldehyde selectivity | 35% | 35% | — |
| Lactic acid concentrtion | 50-80% | 29% | 30% |
| LHSV | 3 h−1 | 3 h−1 | |

| Criteria | (Applied Catalysis A: General 396 (2011) 194-200 | Engineering Science Paper |
|---|---|---|
| Title | EFFECTIVE AND SELECTIVE CONVERSION OF METHYL LACTATE TO ACRYLIC ACID USING $Ca_3(PO_4)_2$—$Ca_2(P2O_7)$ COMPOSITE CATALYST | RESEARCH ON MICROWAVE ASSISTED DEHYDRATION OF LACTIC ACID TO ACRYLIC ACID |
| Catalyst | $Ca_3(PO_4)_2$; $Ca_3(PO_4)_2$—$Ca_2(P2O_7)$ | $Ca_3(PO_4)_2$ + $Na_2HPO_4$ ($Na_2HPO_4$ used as promoter) |
| Process | Catalyst was tested in quartz fixed-bed reactor of 8 mm inner diameter ↓ Catalyst (4 g) was charged in the middle section of the reactor with quartz wool packed in both ends ↓ | — |

-continued

| | PCT1216 | |
|---|---|---|
| | Catalyst preheated at 400° C. for 1 h under high $N_2$ ↓ Feedstock (50 wt % lactic acid aqueous solution) pumped into preheating zone and vapors was driven through the catalyst bed by nitrogen | |
| Acrylic Acid Selectivity | 39 | |
| Conversion % | 98 | 65.8% (yield) |
| Acetaldehyde selectivity | 31 | — |
| Lactic acid concentrtion | 50% | 25% |
| LHSV | 0.175 | |

Advantages of the Invention
1. The process provides for 100% conversion of lactic acid.
2. The process is capable of converting high concentrations of lactic acid.
3. The process leads to minimal production of side products such as acetaldehyde.
4. The catalyst is promoter free.

We claim:

1. A process for dehydrating lactic acid to acrylic acid in a quartz fixed bed reactor, with 100% conversion of lactic acid and at least 50% selectivity for acrylic acid, comprising a stable calcium phosphate as dehydrating catalyst wherein the catalyst has a calcium to phosphorous ratio varying in the range of 1.5 to 1.9, and is optionally modified with 5 wt % sodium, the process comprising the steps of:

i. preheating the catalyst in a fixed-bed reactor at a temperature in the range of 370 to 380° C. for 20 to 40 minute under nitrogen;

ii. preheating a 50-80 wt % lactic acid solution to obtain a lactic acid vapor;

iii. passing the lactic acid vapor in a stream of nitrogen through the catalyst bed in the fixed-bed reactor to obtain a product stream; and iv. condensing the acrylic acid from the product stream.

2. The process as claimed in claim 1, wherein source of the sodium used is selected from the group consisting of $Na_2HPO_4.2H_2O$, $Na_3PO_4.12 H_2O$ or $NaNO_3$.

* * * * *

UNITED STATES PATENT AND TRADEMARK OFFICE
CERTIFICATE OF CORRECTION

PATENT NO. : 8,957,250 B2
APPLICATION NO. : 14/115064
DATED : February 17, 2015
INVENTOR(S) : Mohan Keraba Dongare, Shubhangi Bhalchandra Umbarkar and Samadhan Tanaji Lomate It is certified that error appears in the above-identified patent and that said Letters Patent is hereby corrected as shown below:

ON THE TITLE PAGE

Please change the last name of the second inventor (item 75), from "Umbarker" to -- Umbarkar --.

Signed and Sealed this
Ninth Day of June, 2015

Michelle K. Lee
*Director of the United States Patent and Trademark Office*